(12) United States Patent
Schreiber et al.

(10) Patent No.: US 12,144,724 B2
(45) Date of Patent: Nov. 19, 2024

(54) ACCOMMODATIVE INTRAOCULAR LENS FOR PRODUCING A RESTORING FORCE

(71) Applicant: Carl Zeiss Meditec AG, Jena (DE)

(72) Inventors: Benjamin Schreiber, Berlin (DE); Uwe Wolf, Magdala (DE); André Wolfstein, Berlin (DE); Jan Buchheister, Jena (DE); Hristina Srbinoska, Berlin (DE); Francesca Nicoli, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 18/618,599

(22) Filed: Mar. 27, 2024

(65) Prior Publication Data

US 2024/0238080 A1 Jul. 18, 2024

Related U.S. Application Data

(63) Continuation of application No. PCT/EP2022/075815, filed on Sep. 16, 2022.

(30) Foreign Application Priority Data

Sep. 29, 2021 (DE) .............. 10 2021 125 295.4

(51) Int. Cl.
*A61F 2/16* (2006.01)
(52) U.S. Cl.
CPC .......... *A61F 2/1648* (2013.01); *A61F 2/1635* (2013.01); *A61F 2002/1682* (2015.04); *A61F 2002/16901* (2015.04)
(58) Field of Classification Search
CPC ..... A61F 2/1624; A61F 2/1635; A61F 2/1648
See application file for complete search history.

(56) References Cited

U.S. PATENT DOCUMENTS

| 2003/0204254 A1 | 10/2003 | Peng et al. |
| 2003/0204255 A1 | 10/2003 | Peng et al. |
| 2003/0204256 A1 | 10/2003 | Peng et al. |
| 2010/0179653 A1 | 7/2010 | Argento et al. |
| 2014/0368789 A1* | 12/2014 | Webb ............ A61F 2/1635 359/666 |
| 2018/0161151 A1 | 6/2018 | Honigsbaum |
| 2020/0046490 A1 | 2/2020 | Borja et al. |

(Continued)

FOREIGN PATENT DOCUMENTS

| DE | 603 07 816 T2 | 2/2007 |
| DE | 10 2020 123 518 B3 | 9/2021 |
| EP | 3 829 488 A1 | 6/2021 |

OTHER PUBLICATIONS

International Search Report of the European Patent Office dated Jan. 23, 2023 for international application PCT/EP2022/075815 on which this application is based.

(Continued)

*Primary Examiner* — Jerrah Edwards
*Assistant Examiner* — Jacob Lee Fincher
(74) *Attorney, Agent, or Firm* — Walter Ottesen, P.A.

(57) ABSTRACT

An accommodative intraocular lens is for insertion in the capsular bag of an eye. The accommodative intraocular lens has a first lens part, including a first membrane and an optical axis, and a second lens part which can be detachably coupled to the first lens part, whereby the intraocular lens can be transferred to a coupled state.

13 Claims, 2 Drawing Sheets

(56) References Cited

U.S. PATENT DOCUMENTS

2021/0145569 A1 5/2021 Sergio et al.
2023/0210656 A1 7/2023 Schreiber et al.

OTHER PUBLICATIONS

English translation and International Preliminary Report on Patentability of the European Patent Office dated Jun. 2, 2023 for international application PCT/EP2022/075815 on which this application is based.
English translation and German Office action dated Jun. 28, 2022 for German patent application 10 2021 125 295.4 on which this application is based.
English translation and Written Opinion of the International Searching Authority dated Jan. 23, 2023 for international application PCT/EP2022/075815 on which this application is based.

* cited by examiner

ACCOMMODATIVE INTRAOCULAR LENS FOR PRODUCING A RESTORING FORCE

CROSS-REFERENCE TO RELATED APPLICATIONS

This application is a continuation application of international patent application PCT/EP2022/075815, filed Sep. 16, 2022, designating the United States and claiming priority from German application 10 2021 125 295.4, filed Sep. 29, 2021, and the entire content of both applications is incorporated herein by reference.

TECHNICAL FIELD

The disclosure relates to an accommodative intraocular lens for producing a restoring force.

BACKGROUND

A natural lens of the eye allows objects in the distance and in the vicinity to be seen clearly. This is enabled by virtue of the lens of the eye being able to alter its form and hence the refractive power. The lens of the eye is contained in a capsular bag which is suspended from zonular fibers which, in turn, are connected to a ciliary muscle. When the ciliary muscle relaxes, the zonular fibers tighten, stretching the capsular bag. In the case of a soft lens of the eye, the changing shape of the capsular bag causes the former to also change its shape. As the capsular bag is stretched, the lens of the eye becomes increasingly flattened. This changes the refractive power of the lens of the eye. A flattened lens of the eye leads to a lower refractive power, and so sharp distance vision is possible. This process is reversible, so that when a ciliary muscle is tense, the zonular fibers slacken and the capsular bag is less stretched. Hence, the lens of the eye assumes a shape that is more curved, and so a higher refraction is achieved. This makes it possible to see objects in the vicinity clearly. This variation in the plane of focus is called accommodation.

It is normal for the lens of the eye to lose elasticity with age. The lens of the eye is then less able to change its shape in response to a contraction of the ciliary muscle. This makes it increasingly difficult to focus on close objects. This condition is known as presbyopia. By wearing spectacles or a contact lens, it is possible to compensate for the missing refractive power. With increasing age, however, the lens of the eye becomes increasingly inelastic to hard and can also become cloudy. In medicine, such a condition of the lens of the eye is called a cataract. A spectacle lens cannot compensate for the consequences of clouding the lens of the eye, and so it has become common to remove the clouded lens by surgery. To this end, for example, a needle vibrating with ultrasound is inserted into the eye and the hard and cloudy lens of the eye is comminuted into small particles. This process is known as phacoemulsification. Following such phacoemulsification, the particles are aspirated until the capsular bag has been freed from the natural lens of the eye. To enable good vision again, an artificial lens of the eye is subsequently implanted in the capsular bag. This artificial lens of the eye is called an intraocular lens.

The artificial lens of the eye is usually a lens with a single focal point (monofocal), and so a patient needs spectacles or a contact lens for clear distance and near vision after an artificial lens of the eye has been implanted. However, there are also thoughts of configuring the artificial lens of the eye in such a way that accommodation with a changing plane of focus is possible. Such an artificial lens of the eye is also referred to as an accommodative intraocular lens. Tensing or relaxing a ciliary muscle should make it possible to change the shape of the intraocular lens, and hence its refractive power. It would be desirable to create an artificial lens of the eye which also has similar mechanical properties to the natural lens of the eye.

US 2010/0179653 A1 has disclosed an accommodating intraocular lens. US 2014/0368789 A1 has disclosed an adaptive lens system.

SUMMARY

It is therefore an object of the disclosure to create an accommodative intraocular lens which has similar mechanical properties to a natural lens of the eye.

A first accommodative intraocular lens according to the disclosure for insertion into the capsular bag of an eye includes a first lens part and a second lens part. The first lens part includes a light-transparent lens component including a distal surface of the lens component and a proximal surface of the lens component. Moreover, the first lens part includes a light-transparent first membrane arranged adjacent to the distal surface of the lens component and delimiting a cavity together with the lens component. The first lens part also has an optical axis. The second lens part can be detachably coupled to the first lens part, whereby the intraocular lens is able to be brought into a coupled state in which the second lens part is arranged on a distal side of the first lens part and configured to deform the first membrane by way of a longitudinal displacement of the second lens part parallel to the optical axis. The second lens part includes a first component, which forms a distal end of the second lens part and has an axial through hole in the first component, and a second component, which is configured to deform the first membrane and has an axial through hole in the second component. The optical axis extends through the axial through hole in the first component and through the axial through hole in the second component. The first component and the second component are securely connected to one another at their ends which, in the coupled state, are arranged on the outside in a radial direction with respect to the optical axis, with the first component and the second component being configured to be displaced toward one another in the case of increased stretching of the capsular bag and produce a restoring force as a result.

A second accommodative intraocular lens according to the disclosure for insertion into the capsular bag of an eye includes a first lens part and a second lens part. The first lens part includes a light-transparent lens component including a distal surface of the lens component and a proximal surface of the lens component. Moreover, the first lens part includes a light-transparent first membrane arranged adjacent to the distal surface of the lens component and delimiting a cavity together with the lens component. The first lens part also has an optical axis. The second lens part can be detachably coupled to the first lens part, whereby the intraocular lens is able to be brought into a coupled state in which the second lens part is arranged on a distal side of the first lens part and configured to deform the first membrane by way of a longitudinal displacement of the second lens part parallel to the optical axis. The second lens part includes a first component, which forms a distal end of the second lens part and has an axial through hole in the first component, and a second component, which extends at least as far as the lens component in the direction of the optical axis and has an axial through hole in the second component. The optical axis extends through the axial through hole in the first component and through the axial through hole in the second component. The first component and the second component are securely connected to one another at their ends which, in the coupled state, are arranged on the outside in a radial direction with respect to the optical axis, with the first component and the second component being configured to be displaced toward one another in the case of increased stretching of the capsular bag and produce a restoring force as a result.

The arrangement of the lens component, the cavity and the first membrane is configured to perform optical imaging, whereby the first lens part has the optical axis. An incision is introduced into the capsular bag in order to insert the intraocular lens into the capsular bag of an eye. The first lens part is inserted into the capsular bag via the incision first, followed by the second lens part. The second lens part is arranged in the capsular bag in such a way that the intraocular lens reaches the coupled state. Since the membrane deforms as a result of the longitudinal displacement of the second lens part, the membrane experiences a change in its radius of curvature. The membrane changes its refraction by virtue of the membrane changing its radius of curvature, with the result that an accommodation of the eye to distant or near objects is achievable.

The restoring force arises because the capsular bag experiences increased stretching as a ciliary muscle relaxes. As a result, an anterior region of the capsular bag presses against the first component. In the first intraocular lens according to the disclosure, a posterior region of the capsular bag presses against the second component via the first lens part. In the second intraocular lens according to the disclosure, the second component is in contact with the posterior region of the capsular bag, and so the posterior region of the capsular bag presses directly against the second component. As a result, the first component and the second component are displaced in the direction toward one another, whereby the restoring force arises. The restoring force leads to the capsular bag being stretched less again when the ciliary muscle is tensioned again following the relaxation. As a result, the intraocular lens has similar mechanical properties to a natural lens of the eye.

For the second intraocular lens according to the disclosure, it is preferable that the first component includes a cylindrical portion which, in the coupled state, forms the inner end of the first component in the radial direction and which is in contact with the first lens part.

For the second intraocular lens according to the disclosure, it is preferable that the second component extends at least as far as a proximal side of the first lens part in the axial direction. For the second intraocular lens according to the disclosure, it is also preferable that a proximal surface of the second component has a convexly curved embodiment. As a result, the posterior region of the capsular bag can nestle closely against the second component, whereby injury to the tissue of the posterior region of the capsular bag as a result of the second component can be avoided.

For both intraocular lenses according to the disclosure, it is preferable that the first component and/or the second component have a maximum extent of at least 8.5 mm in the radial direction. As a result, it is possible to laterally distend and keep open the capsular bag, both in a non-stretched state and in a stretched state. As a result, injury to the tissue of the capsular bag can be prevented. For example, the maximum extent can be at most 10.0 mm.

For both intraocular lenses according to the disclosure, it is preferable that the lens component is a second membrane or an optic body.

For both intraocular lenses according to the disclosure, Young's modulus of the first component and of the second component is preferably from 1.5 MPa to 5.0 MPa. For both intraocular lenses according to the disclosure, Young's modulus of the first membrane and/or of the second membrane is preferably no more than 3 MPa, in particular from 1.5 MPa to 2.0 MPa.

For both intraocular lenses according to the disclosure, it is preferable that the second lens part includes a further lens. In this context, it is particularly preferable that an optical axis of the further lens substantially coincides with the optical axis of the first lens part. For example, the further lens can be toric. This can advantageously correct an astigmatism. It is also conceivable for the further lens to have a non-accommodative embodiment.

For both intraocular lenses according to the disclosure, a distal surface of the first component preferably has a convexly curved embodiment. As a result, the surface of the first component in contact with the capsular bag has the shape of the capsular bag. As a result, the anterior region of the capsular bag can nestle particularly closely against the first component, whereby injury to the tissue of the capsular bag as a result of the first component can be avoided.

For both intraocular lenses according to the disclosure, the first component and/or the second component preferably has a plurality of radial through holes, through which a liquid is able to flow from an inner side of the second lens part in the radial direction to an outer side of the second lens part in the radial direction. By virtue of the radial through holes leading to more flow in the capsular bag than in the case without the radial through holes, this can reduce the probability of occurrence of a secondary cataract.

For both intraocular lenses according to the disclosure, it is preferable that the second lens part includes a plurality of feet which, in an axial region, form the outer end of the second lens part in the radial direction, protrude from the remaining second lens part in a proximal direction and are arranged adjacent to one another in a circumferential direction with respect to the optical axis. The feet allow a particularly large region of the capsular bag to be distended and, as a result of the feet being arranged at a distance from one another, a flow is possible between the feet, whereby the probability of occurrence of a secondary cataract is reduced. The feet are particularly preferably configured to retain the first lens part, in particular the lens component, in the coupled state and hence center the first lens part in relation to the second lens part. To this end, the feet may be configured for example rotationally symmetrically with respect to the optical axis.

BRIEF DESCRIPTION OF DRAWINGS

The invention will now be described with reference to the drawings wherein.

DETAILED DESCRIPTION

Figure 1:
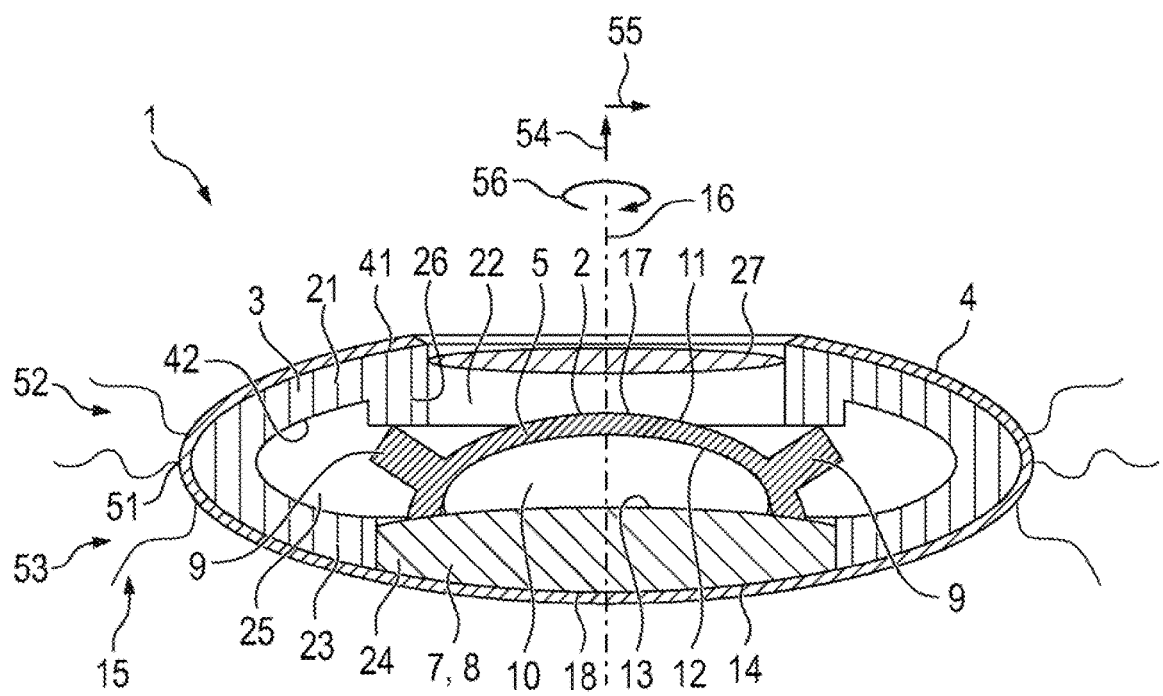
FIG. 1 shows a longitudinal section through a first embodiment of the accommodative intraocular lens according to the disclosure in a capsular bag which is in a non-stretched state.
Figure 2:
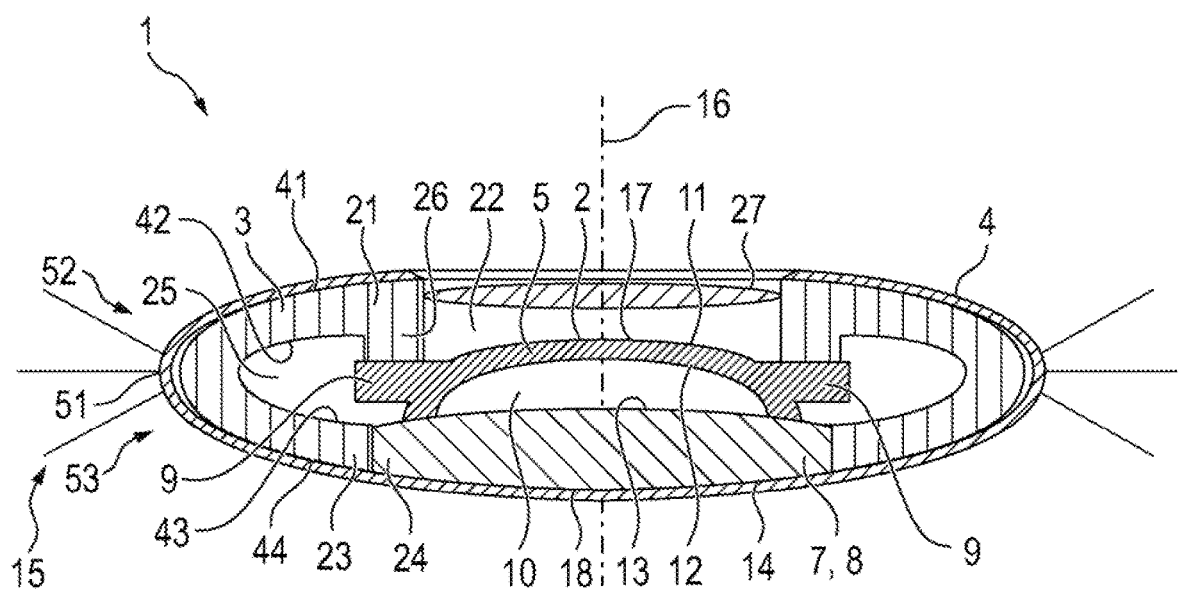
FIG. 2 shows a longitudinal section through the intraocular lens according to FIG. 1, wherein the capsular bag is in a stretched state.

FIGS. 1 and 2 show that, according to a first embodiment of the accommodative intraocular lens 1 for insertion into the capsular bag 4 of an eye, the intraocular lens 1 includes a first lens part 2 and a second lens part 3. The first lens part 2 includes a light-transparent lens component 7 including a distal surface 13 of the lens component 7 and a proximal surface 14 of the lens component 7, a light-transparent first membrane 5 arranged adjacent to the distal surface 13 of the lens component 7 and delimiting a cavity 10 together with the lens component 7, and an optical axis 16. The second lens part 3 can be detachably coupled to the first lens part 2, whereby the intraocular lens 1 is able to be brought into a coupled state in which the second lens part 3 is arranged on a distal side 17 of the first lens part 2 and configured to deform the first membrane 5 by way of a longitudinal displacement of the second lens part 3 parallel to the optical axis 16. The second lens part 3 includes a first component 21, which forms a distal end of the second lens part 3 and has an axial through hole 22 in the first component 21, and a second component 23, which extends at least as far as the lens component 7 in the axial direction 54 with respect to the optical axis 16 and has an axial through hole 24 in the second component 23. The optical axis 16 extends through the axial through hole 22 in the first component 21 and through the axial through hole 24 in the second component 23. The first component 21 and the second component 23 are securely connected to one another at their ends which, in the coupled state, are arranged on the outside in a radial direction 55 with respect to the optical axis 16, with the first component 21 and the second component 23 being configured to be displaced toward one another in the case of increased stretching of the capsular bag 4 and produce a restoring force as a result.

Figure 3:
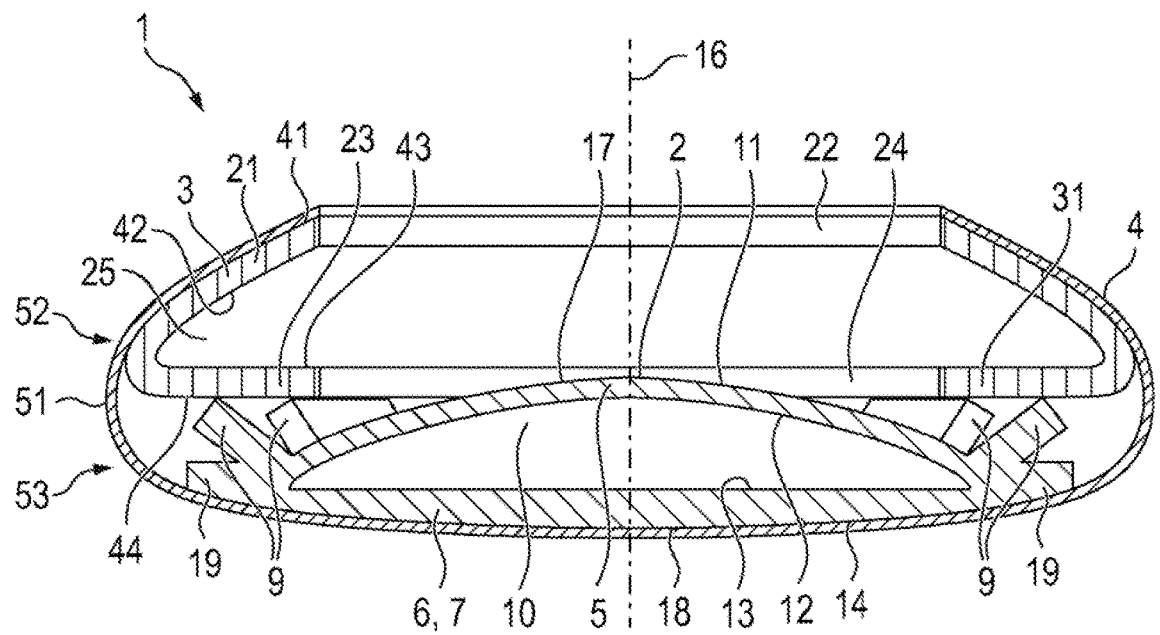
FIG. 3 shows a longitudinal section through a second embodiment of the accommodative intraocular lens according to the disclosure; and, FIG. 4 shows a longitudinal section through a third embodiment of the accommodative intraocular lens according to the disclosure.
Figure 4:
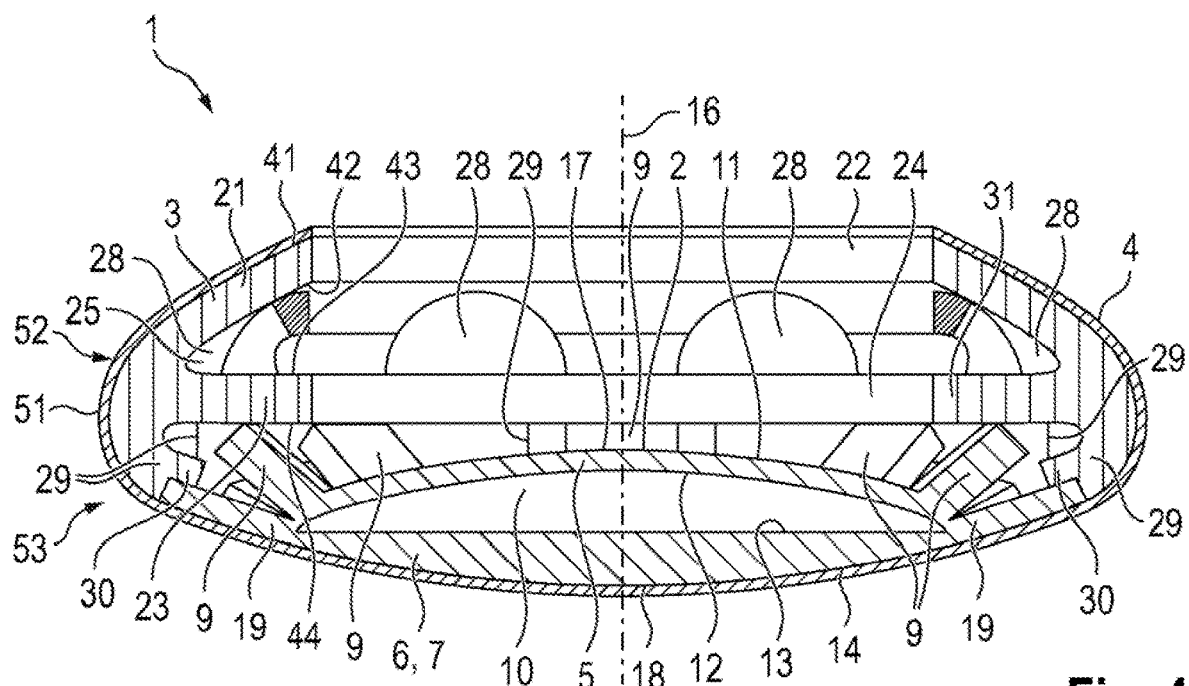

As evident from FIGS. 3 and 4, the intraocular lens 1 includes a first lens part 2 and a second lens part 3 according to a second and third embodiment of an accommodative intraocular lens 1 for insertion into the capsular bag 4 of an eye. The first lens part 2 includes a light-transparent lens component 7 including a distal surface 13 of the lens component 7 and a proximal surface 14 of the lens component 7, a light-transparent first membrane 5 arranged adjacent to the distal surface 13 of the lens component 7 and delimiting a cavity 10 together with the lens component 7, and an optical axis 16. The second lens part 3 can be detachably coupled to the first lens part 2, whereby the intraocular lens 1 is able to be brought into a coupled state in which the second lens part 3 is arranged on a distal side 17 of the first lens part 2 and configured to deform the first membrane 5 by way of a longitudinal displacement of the second lens part 3 parallel to the optical axis 16. The second lens part 3 includes a first component 21, which forms a distal end of the second lens part 3 and has an axial through hole 22 in the first component 21, and a second component 23, which is configured to deform the first membrane 5 and has an axial through hole 24 in the second component 23. The optical axis 16 extends through the axial through hole 22 in the first component 21 and through the axial through hole 24 in the second component 23. The first component 21 and the second component 23 are securely connected to one another at their ends which, in the coupled state, are arranged on the outside in a radial direction 55 with respect to the optical axis 16, with the first component 21 and the second component 23 being configured to be displaced toward one another in the case of increased stretching of the capsular bag 4 and produce a restoring force as a result.

FIG. 1 depicts the capsular bag 4 in a non-stretched state, in which zonular fibers 15 attached to the capsular bag 4 have become slack. FIG. 2 shows that a ciliary muscle (not depicted) slackening leads to tightening of the zonular fibers 15, whereby the capsular bag 4 reaches a stretched state. As a result, an anterior region 52 of the capsular bag 4 presses against the first component 21. A posterior region 53 of the capsular bag 4 presses against the second component 23, wherein, according to the first embodiment, the posterior region 53 of the capsular bag 4 presses directly against the first component 21 and, according to the second embodiment and the third embodiment, the posterior region 53 presses indirectly against the second component 23 via the first lens part 2. As a result, the first component 21 and the second component 23 are displaced toward one another, whereby the restoring force is produced. When the zonular fibers 15 slacken again as a result of a tensioning of the ciliary muscle, the capsular bag 4 returns to the non-stretched state according to FIG. 1 on account of the restoring force.

As evident from FIGS. 1 and 2, the first component 21 may, according to the first embodiment, include a cylindrical portion 26 which, in the coupled state, forms the inner end of the first component 21 in the radial direction 55 and which is in contact with the first lens part 2. In this case, the cylindrical portion 26 may protrude from the remaining first component 21 toward the first lens part 2 in an axial direction 54 with respect to the optical axis 16.

FIGS. 1 and 2 show that, according to the first embodiment, the second component 23, when in the coupled state, may extend at least as far as a proximal side 18 of the first lens part 2 in the axial direction 54. It is also evident that a proximal surface 44 of the second component 23 may have a convexly curved embodiment.

According to the second embodiment and the third embodiment, the second component 23 may include a slice-shaped portion 31 which is in contact with the first lens part 2 and which delimits the axial through hole 24 in the second component 23; compare FIGS. 3 and 4. In the coupled state, the slice-shaped portion 31 and the first component 21 may delimit an intermediate space 25 of the second lens part 3 in the axial direction 54. The intermediate space 25 can be inwardly open in the radial direction.

It is true for all embodiments that the first component 21 and/or the second component 23 are able to extend as far as an equator 51 of the capsular bag 4, with the equator 51 separating an anterior region 52 of the capsular bag 4 from a posterior region 53 of the capsular bag. To this end, the first component 21 and/or the second component 23 may have a maximum extent of at least 8.5 mm in the radial direction 55. For example, the maximum extent in the radial direction 55 can be at most 10.0 mm.

As evident from FIGS. 1 to 4, the first lens part 2 may include a plurality of bending elements 9, which are arranged at the distal surface 11 of the first membrane 5 and which are arranged spaced apart from one another in the circumferential direction 56 with respect to the optical axis 16. In the first embodiments, the bending elements 9 are in contact with the first component 21, in particular with the cylindrical portion 26. In the second and third embodiment, the bending elements 9 are in contact with the second component 23.

FIGS. 1 and 2 show that the lens component 7 can be an optic body 8, for example. FIGS. 3 and 4 show that the lens component 7 can be a second membrane 6, for example.

Young's modulus of the first component 21 and of the second component 23 can be from 1.5 MPa to 5.0 Pa. Young's modulus of the first membrane 5 and/or of the second membrane 6 can be no more than 3 MPa, in particular from 1.5 MPa to 2 MPa.

FIGS. 1 and 2 show that the second lens part 3 may include a further lens 27. In this context, the optical axis of the further lens 27 may substantially coincide with the optical axis 16 of the first lens part 2 in the coupled state. For example, the further lens 27 can be toric. As a result, an astigmatism can be corrected by means of the further lens. Moreover, it is conceivable for the further lens 27 to have a non-accommodative embodiment; that is, it cannot change its refractive power in contrast with the first lens part 2.

It is evident from FIGS. 1 to 4 that a distal surface 41 of the first component 21 may have a convexly curved embodiment.

FIG. 4 shows that the first component 21 and/or the second component 23 may have a plurality of radial through holes 28, through which a liquid is able to flow from an inner side of the second lens part 3 in the radial direction 55 to an outer side of the second lens part 3 in the radial direction 55.

FIG. 4 also shows that the second lens part 3 may include a plurality of feet 29 which, in an axial region, form the outer end of the second lens part 3 in the radial direction 55, protrude from the remaining second lens part 3 in a proximal direction and are arranged adjacent to one another in a circumferential direction 56 with respect to the optical axis 16. The feet 29 can be configured to retain the first lens part 2, in particular the lens component 7, in the coupled state and hence center the first lens part 2 in relation to the second lens part 3. For centering purposes, the feet 29 may be arranged for example rotationally symmetrically with respect to the optical axis 16. To retain the first lens part 2, the feet 29 may each have a radial projection 30, which protrudes from the feet 29 in the direction of the optical axis 16. The radial projection 30 may be configured to clamp the first lens part 2, in particular a haptic 19 of the first lens part 2, between the radial projection 30 and the capsular bag 4 in the coupled state.

It is understood that the foregoing description is that of the preferred embodiments of the invention and that various changes and modifications may be made thereto without departing from the spirit and scope of the invention as defined in the appended claims.

LIST OF REFERENCE SIGNS

1 Accommodative intraocular lens
2 First lens part
3 Second lens part
4 Capsular bag
5 First membrane
6 Second membrane
7 Lens component
8 Optic body
9 Bending element
10 Cavity
11 Distal surface of the first membrane
12 Proximal surface of the first membrane
13 Distal surface of the lens component
14 Proximal surface of the lens component
15 Zonular fibers
16 Optical axis
17 Distal side of the first lens part
18 Proximal side of the first lens part
19 Haptic
21 First component
22 Axial through hole in the first component
23 Second component
24 Axial through hole in the second component
25 Intermediate space
26 Cylindrical portion
27 Further lens
28 Radial through hole
29 Foot
30 Radial projection
31 Slice-shaped portion
41 Distal surface of the first component
42 Proximal surface of the first component
43 Distal surface of the second component
44 Proximal surface of the second component
51 Equator of the capsular bag
52 Anterior region of the capsular bag
53 Posterior region of the capsular bag
54 Axial direction
55 Radial direction
56 Circumferential direction

The invention claimed is:

1. An accommodative intraocular lens for insertion into the capsular bag of an eye, the accommodative intraocular lens comprising:
    a first lens part including a light-transparent lens component having a distal surface of said light-transparent lens component and a proximal surface of said light-transparent lens component;
    said first lens part further including a light-transparent first membrane arranged adjacent to said distal surface of said light-transparent lens component and delimiting a cavity together with said light-transparent lens component;
    said first lens part defining an optical axis;
    a second lens part configured to be detachably coupled to said first lens part, whereby the accommodative intraocular lens is able to be brought into a coupled state in which said second lens part is arranged on a distal side of said first lens part and configured to deform said first membrane by way of a longitudinal displacement of said second lens part parallel to said optical axis;
    said second lens part including a first component, which forms a distal end of the second lens part and has an axial through hole in said first component, and a second component, which extends at least as far as the lens component in an axial direction with respect to said optical axis and defines an axial through hole in said second component, with said optical axis extending through said axial through hole in said first component and through said axial through hole in said second component;
    said first component and said second component being securely connected to one another at their ends which, in said coupled state, are arranged outside in a radial direction with respect to the optical axis; and,
    said first component and said second component being configured to be displaced toward one another in a case of increased stretching of the capsular bag and produce a restoring force as a result.

2. The intraocular lens of claim 1, wherein said first component includes a cylindrical portion which, in said coupled state, forms an inner end of said first component in the radial direction and which is in contact with said first lens part.

3. The intraocular lens of claim 1, wherein said second component, in said coupled state, extends at least as far as a proximal side of said first lens part in the axial direction.

4. The intraocular lens of claim 3, wherein a proximal surface of said second component has a convexly curved configuration.

5. The intraocular lens of claim 1, wherein at least one of said first component and said second component have a maximum extent of at least 8.5 millimeters in the radial direction.

6. The intraocular lens of claim 1, wherein a Young's modulus of said first component and of said second component is from 1.5 MPa to 5.0 MPa.

7. The intraocular lens of claim 1, wherein a distal surface of said first component has a convexly curved configuration.

8. The intraocular lens of claim 1, wherein said second lens part includes a further lens.

9. The intraocular lens of claim 8, wherein said further lens is at least one of: a toric configuration and a non-accommodative configuration.

10. The intraocular lens of claim 1, wherein at least one of said first component and said second component defines a plurality of radial through holes through which a liquid is able to flow from an inner side of said second lens part in the radial direction to an outer side of said second lens part in the radial direction.

11. The intraocular lens of claim 1, wherein said second lens part includes a plurality of feet which, in an axial region, form an outer end of said second lens part in the radial direction, protrude from a remaining second lens portion in a proximal direction and are arranged mutually adjacent in a circumferential direction with respect to said optical axis.

12. The intraocular lens of claim 11, wherein said feet are configured to retain said first lens part in the coupled state and consequently center said first lens part in relation to said second lens part.

13. The intraocular lens of claim 11, wherein said feet are configured to retain said lens component in the coupled state and consequently center said first lens part in relation to said second lens part.

* * * * *